United States Patent
Roskin et al.

Patent Number: 5,823,953
Date of Patent: Oct. 20, 1998

[54] SECRETION ANALYSIS APPARATUS AND METHOD

[76] Inventors: Amy C. Roskin, 8110 Royal Palm Blvd. Ste. 108, Coral Springs, Fla. 33065; Joanne M. Richards, Box 770041, Coral Springs, Fla. 33077

[21] Appl. No.: 667,078

[22] Filed: Jun. 20, 1996

[51] Int. Cl.$^6$ .................................................. A61B 5/00
[52] U.S. Cl. .................. 600/367; 600/309; 600/584; 600/573; 604/358; 604/362
[58] Field of Search .................. 128/632, 636, 128/630, 771, 760; 604/358, 362, 367; 422/58, 65, 68.1, 163, 906

[56] References Cited

U.S. PATENT DOCUMENTS

| | | |
|---|---|---|
| 2,664,879 | 1/1954 | Hardy . |
| 3,509,872 | 5/1970 | Truhan . |
| 5,063,930 | 11/1991 | Nucci . |
| 5,217,444 | 6/1993 | Schoenfeld ............................ 604/358 |
| 5,275,591 | 1/1994 | Mavinkurve ........................... 604/389 |
| 5,425,377 | 6/1995 | Caillouette . |
| 5,445,147 | 8/1995 | Schoendorfer et al. ................ 128/632 |

FOREIGN PATENT DOCUMENTS 3261452 11/1991 Japan ..................................... 128/636

Primary Examiner—Jennifer Bahr
Assistant Examiner—Rosiland Kearney
Attorney, Agent, or Firm—Alvin S. Blum

[57] ABSTRACT

A method and device for distinguishing between yeast infection and other secretion-causing conditions makes use of the observation that secretions caused by yeast infection generally have a pH of less than about 4.5, whereas most other conditions cause less acid secretions. The device is for use by the woman having the secretions and does not involve introducing anything into the body nor does it require special skills or training. A material that indicates pH by a color change is mounted on a catamenial pad, pantyliner or the like worn on the body so as to be wetted by the secretions draining from the vagina. Observation of the color of the wetted material enables the user, by simple comparison to a color chart, to determine whether she has a yeast infection that is treatable by medicine available without medical prescription or whether she should instead see a physician because yeast treatment would be ineffectual and would delay proper treatment.

15 Claims, 1 Drawing Sheet

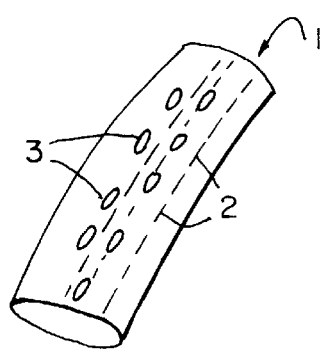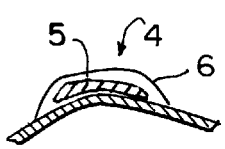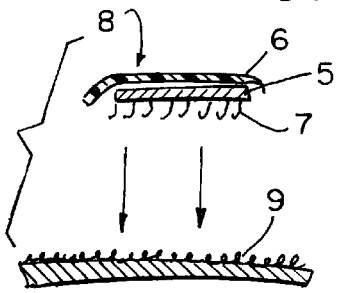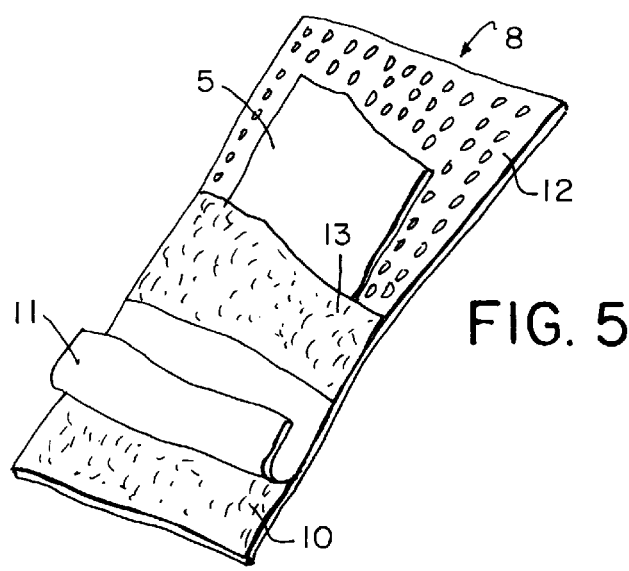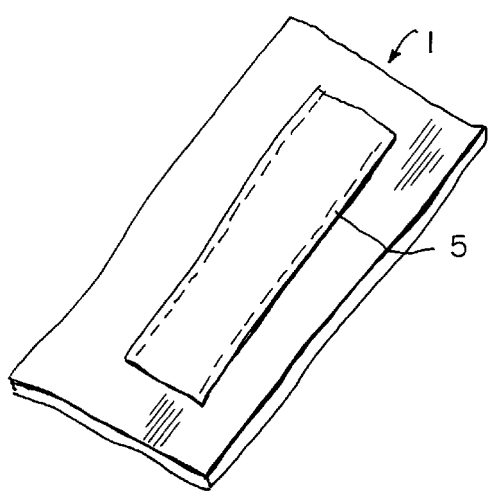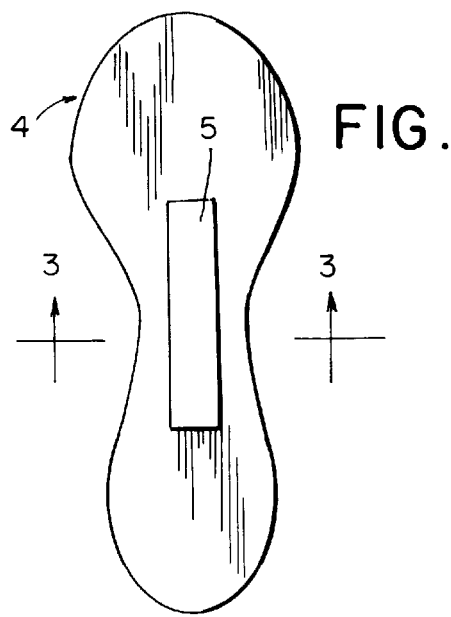

2

SECRETION ANALYSIS APPARATUS AND METHOD

BACKGROUND OF THE INVENTION

1. Field of the Invention

This invention relates to diagnosis of infection and more particularly to a method and apparatus for external measurement of the pH of vaginal secretion.

2. Background Art

Vaginal infections may be divided into two general categories, yeast infections which cause acid secretions with a pH below about 4.5 and non-yeast infections which cause secretions with a pH generally above 4.5.

A number of over the counter medicines are now available for treatment of vaginal yeast infections. The signs and symptoms of yeast infections are not readily distinguishable from other infections, although they comprise less than half of the infections. Consequently, patients too often resort to self treatment with yeast medicine when it cannot possibly be effective. This may dangerously delay effective treatment.

U.S. Pat. No. 2,664,879 issued Jan. 5, 1954 to Hardy and U.S. Pat. No. 5,063,930 issued Nov. 12, 1991 to Nucci disclose devices for measuring vaginal pH internally with pH indicators carried on an instrument inserted into the vagina.

These have several disadvantages. Women generally object to any internal instrumentation. The sensitive tissues are vulnerable to reaction with many materials such as indicators. Sterility is a further concern. They do not lend themselves to home health care in conjunction with the over the counter medicine used for yeast infections.

SUMMARY OF THE INVENTION

It is accordingly an object of the invention to provide a method and apparatus for differentiating between yeast and non yeast vaginal infections that is more acceptable to women, safer, easier to use, and less expensive to produce.

The infections produce secretions which drain from the vagina. We have discovered that measurement of the pH of the secretions after they have left the body will effectively differentiate the two types of infections. Women are accustomed to absorbing fluids escaping from the vagina with catamenial pads, panty liners, and the like. The invention comprises pH indicating material attached or attachable to garments or devices ordinarily worn so as to absorb secretions. The pH indicating material is of the type that provides a color indicative of the pH of the fluid contacting it. This enables an untrained user to determine the pH of the secretions by simple visual reference to a color chart. There is less exposure to sensitive tissues for infection and toxicity problems.

These and other objects, features and advantages of the invention will become more apparent when the detailed description is studied in conjunction with the drawings in which like reference characters indicate like elements in the various figures.

BRIEF DESCRIPTION OF THE DRAWINGS

FIG. 1 is perspective view of a pad of the invention.

FIG. 2 is a perspective view of a pantyliner embodying the invention.

FIG. 3 is a sectional view taken through line 3—3 of FIG. 2.

FIG. 4 is a sectional view of another embodiment of the invention.

FIG. 5 is a perspective view of another embodiment of the invention, with various layers partially broken away.

FIG. 6 is a perspective view of another pad of the invention.

DETAILED DESCRIPTION OF PREFERRED EMBODIMENTS

Referring now first to FIG. 1, a catamenial pad 1 may be of the type in common use or a thinner pad especially made for this purpose. Fibers or threads 2 comprised of pH indicating material such as cotton thread impregnated with pH indicating dye may be sewn onto the pad surface where they will become wetted by the vaginal secretions and change color to thereby disclose to the user the pH of the secretions. The pH indicator indicating pH at least in the range of pH 3.5–5.5. A color chart (not shown) may be included, such as on the wrapper, for comparison, along with instructions such as "this color indicates that your problem is not a yeast infection, see your doctor". Alternatively, spots of the dye 3 may be directly imprinted on the pad.

Referring now to FIGS. 2 and 3, a pantyliner of the invention comprises a conventional pantyliner 4 upon whose surface is securely attached a pH indicating paper strip 5. An overlay of a thin, transparent, water permeable and water insoluble plastic film 6 holds the strip in place and separates the strip from any sensitive body tissues that might react unfavorably to the pH indicating material. The secretions will diffuse through the film 6 and wet the indicating strip 5 to provide the color change visible through the transparent film. An example of a suitable film material would be ethylcellulose which is inert enough to be acceptable for oral medications.

Referring now to FIG. 4, a pH indicating strip 5, coated with a transparent, water permeable, water insoluble film 6 has affixed to the underside a layer of hook material 7 of the hook and loop fastener type that enables the combined device 8 to be attachable and detachable from a soft fabric having a loose surface texture 9 which may serve as the loop material for attachment. Certain garments, pads and pantyliners may have a texture of this nature without modification.

FIG. 5 shows another attachable, detachable pH indicating strip 8 having a pressure sensitive adhesive surface 10 protected with release paper 11. The release paper is stripped off and the strip 8 is removably adhered to the crotch of an undergarment. The indicating paper strip 5 is sandwiched between two layers of transparent plastic film, the outer, perforated film layer 12 and the inner film layer 13 that is carrying the adhesive. The perforations permit penetration of the secretions into the paper strip 5 while keeping the dye away from sensitive tissues.

FIG. 6 shows a catamenial pad 1 in which the pH indicating strip 5 is stitched in place.

The above disclosed invention has a number of particular features which should preferably be employed in combination although each is useful separately without departure from the scope of the invention. While we have shown and described the preferred embodiments of our invention, it will be understood that the invention may be embodied otherwise than as herein specifically illustrated or described, and that certain changes in the form and arrangement of parts and the specific manner of practicing the invention may be made within the underlying idea or principles of the invention.

What is claimed is:

1. A self-diagnostic method of diffentiating a vaginal yeast infection from other secretion causing conditions, the method comprising the steps of:

wearing an external device on the body positioned to receive secretions that have drained from the vagina, the device having means for indicating by a visual color change the pH of the secretions received thereon;

removing the device after vaginal secretions have been received thereon after draining from the vagina;

observing the color of the device;

determining from the color whether the pH is greater than about 4.5 in which case the secretions are not indicative of a yeast infection, or less than about 4.5 in which case the secretions are indicative of a yeast infection.

2. The method according to claim 1, in which the external device is a catamenial pad.

3. The method according to claim 1, in which the external device is a pantyliner.

4. A device for self-diagnostic use for distinguishing between a yeast infection causing vaginal secretions and other secretion causing conditions, the device comprising:

a structure having an outer layer and an inner layer;

a pH indicating material at or adjacent said outer layer for indicating by color the pH at least in the range of about pH 3.5–5.5 of liquids wetting the material; and means for mounting the structure external to the body to receive thereon, and be wetted by, secretions that have drained from the vagina, whereby a color indication of pH of less than about 4.5 is indicative of a yeast infection, and so positioned that the inner layer is substantially occluded from atmospheric vaporization, such as by a wearer's thighs and by a seat when the wearer is seated or a plastic barrier film, so that there is insubstantial loss of water and volatiles from the secretions that would alter indicated pH.

5. The device according to claim 4, in which the means for mounting is adhesive.

6. The device according to claim 4, in which the means for mounting comprises hook material.

7. The device according to claim 4, in which the means for mounting comprises stitching.

8. The device according to claim 4 further comprising a water permeable barrier film over the pH indicating material for protective separation of the pH indicating material from direct contact with the body.

9. The device according to claim 4, in which the pH indicating material is in the form of fibers or threads stitched onto a wearable substrate.

10. The device according to claim 9, in which the substrate is selected from the group consisting of pantyliners and catamenial pads.

11. The device according to claim 4, in which the pH indicating material comprises dye imprinted on a wearable substrate.

12. The device according to claim 10, in which the wearable substrate is selected from the group consisting of pantyliners and catamenial pads.

13. The device according to claim 4 in the form of a catamenial pad.

14. The device according to claim 4 in the form of a pantyliner.

15. The device according to claim 4 further comprising a transparent perforated barrier film on the outer layer over the pH indicating material for protective separation of the pH indicating material from direct contact with the body while passing therethrough the secretions and an imperforate barrier film on the inner layer.

* * * * *